United States Patent

Dangelmayer et al.

Patent Number: 5,691,875
Date of Patent: Nov. 25, 1997

[54] SYSTEMS FOR PREVENTING ELECTROSTATIC ACCUMULATION

[75] Inventors: George Theodore Dangelmayer, Plaistow, N.H.; John Phillip Franey, Bridgewater; Robert Garland Renninger, II, Glen Gardner, both of N.J.

[73] Assignee: Lucent Technologies Inc., Murray Hill, N.J.

[21] Appl. No.: 311,689

[22] Filed: Sep. 23, 1994

[51] Int. Cl.⁶ .................................................. H05F 3/02
[52] U.S. Cl. ................................. 361/222; 361/220
[58] Field of Search .............................. 361/212, 220, 361/222, 223, 224

[56] References Cited

U.S. PATENT DOCUMENTS

| | | | |
|---|---|---|---|
| 3,416,033 | 12/1968 | Hoover et al. | 361/212 |
| 3,711,742 | 1/1973 | Pinkham, Jr. | |
| 3,912,973 | 10/1975 | Young | 361/224 |
| 4,313,148 | 1/1982 | Turner | 361/212 |
| 4,398,277 | 8/1983 | Christiansen et al. | |
| 4,459,633 | 7/1984 | Vandermark | 361/220 |
| 4,551,783 | 11/1985 | Cohen et al. | 361/223 |
| 4,570,200 | 2/1986 | Osada et al. | 361/212 |
| 4,605,988 | 8/1986 | Nienhuis et al. | |
| 4,633,364 | 12/1986 | Nakamura et al. | 361/216 |
| 4,649,374 | 3/1987 | Hoigaard | |
| 4,654,748 | 3/1987 | Rees | |
| 4,664,158 | 5/1987 | Sands | |
| 4,677,520 | 6/1987 | Price | |
| 4,677,521 | 6/1987 | Frazier | |
| 4,680,668 | 7/1987 | Belkin | |
| 4,698,724 | 10/1987 | Burvee | |
| 4,722,025 | 1/1988 | Robinson | |
| 4,745,517 | 5/1988 | Pitts | 361/212 |
| 4,745,519 | 5/1988 | Breidegam | |
| 4,762,497 | 8/1988 | Burvee | |
| 4,810,418 | 3/1989 | Burvee | |
| 4,847,729 | 7/1989 | Hee | |
| 4,859,992 | 8/1989 | Hoigaard | |
| 4,868,710 | 9/1989 | Powell | 361/220 |
| 4,885,728 | 12/1989 | Gosselin | |
| 5,004,425 | 4/1991 | Hee | 361/220 |
| 5,032,948 | 7/1991 | Klepel | 361/220 |
| 5,083,367 | 1/1992 | Klepel | |
| 5,154,886 | 10/1992 | Franey et al. | |
| 5,196,985 | 3/1993 | Ford et al. | |
| 5,511,840 | 4/1996 | Allison et al. | 361/220 |

FOREIGN PATENT DOCUMENTS

| | | | |
|---|---|---|---|
| 0055246 | 6/1982 | European Pat. Off. | |
| 0-067922 | 12/1982 | European Pat. Off. | A61N 1/14 |
| 2524806 | 10/1983 | France | 361/212 |
| 2688973 | 9/1993 | France | 361/212 |
| 87 09 107 U | 10/1987 | Germany | |
| 3617734 A1 | 12/1987 | Germany | |
| WO-A-94 04012 | 2/1994 | WIPO | H05F 3/02 |

OTHER PUBLICATIONS

"Method for Providing Electrostatic Discharge Keyboards", Anonymous, Research Disclosure, No. 313, p. 414, Emsworth, GB (May 1990).

*Primary Examiner*—Fritz Fleming
*Attorney, Agent, or Firm*—Richard J. Botos

[57] ABSTRACT

The present invention provides a grounding system for discharging static electricity. The grounding system includes a body-contacting member which forms an electrical connection with at least a portion of a human body and a grounding cable. The grounding cable has an elongated conductive member with a first end for connection to ground potential and a second end for electrically communicating with the body-contacting member. At least one end of the elongated conductive member is embedded within a resistive material having an electrical conductivity of $10^5$–$10^{12}$ ohms/square. In one embodiment, the body-contacting member is a wrist or ankle strap while the resistive material is a polymer loaded with conductive and semiconductive particles. Exemplary conductive particles are selected from carbon, metals, and mixtures thereof.

5 Claims, 3 Drawing Sheets

5,691,875

SYSTEMS FOR PREVENTING ELECTROSTATIC ACCUMULATION

FIELD OF THE INVENTION

The present invention relates to systems and devices for controlling electrostatic charge accumulation and, more particularly, to systems which prevent uncontrolled discharge of static electricity.

BACKGROUND OF THE INVENTION

Accumulation of electrostatic charges is problematic during fabrication of static sensitive devices (SSDs). Humans can charge to potentials in excess of 20,000 volts through triboelectric processes, i.e., friction-induced static build-up or through interaction with electric fields. Uncontrolled discharge of static electricity causes painful shocks and leads to failure of sensitive semiconductor devices and integrated circuits during their manufacture. Additionally, sudden discharge creates fire or explosion hazards for personnel working with flammable or combustible substances.

During fabrication of SSDs, industry standards require workers to continually dissipate static electricity by providing a safe ground path. Usually, this ground path is provided through a conductive cable connected at one end to ground and at the other end to a wrist or ankle strap in electrical contact with the worker. To increase worker safety, a resistor is positioned in the ground path adjacent the wrist or ankle strap. The resistor slows the rate of electrostatic discharge and prevents electrical injury to the worker in the event that the ground path inadvertently contacts a voltage source. Personnel who come into contact with SSDs are required to electrically test their grounding strap prior to entry into a protected area. This check is recorded and audited by ISO (International Standards Organization) inspectors.

Current grounding strap designs frequently fail at the connection point between the resistor and the grounding wire. Since the resistor is embedded in a polymer encapsulant, this failure is not immediately observable. By the time the failure is discovered, the worker wearing the flawed grounding strap can have damaged numerous SSDs.

In situations in which workers are exposed to electrical fields, it is also desirable to dissipate accumulated static electricity to prevent painful shocks and minimize the risk of equipment damage from sudden electrostatic discharge. For example, telephone operators experience charge coupling when seated at video display terminals. This charge coupling creates an accumulation of static electricity on the operator. Uncontrolled discharge of this static electricity is experienced as a painful shock through the telephone headset to the grounding wire of the telephone.

There is a need in the art for improved reliability in grounding mechanisms for workers, particularly for those employed in static sensitive device manufacture. There is a further need in the art for grounding devices which, in the event of failure, provide readily observable failure modes. There is a further need for grounding systems which can be readily employed in a variety of apparatus to prevent accumulation of static electricity. Such grounding systems could be used to prevent uncontrolled static discharge resulting in painful shocks or device damage.

SUMMARY OF THE INVENTION

The present invention provides a grounding system for discharging static electricity. The grounding system includes a body-contacting member which forms an electrical connection with at least a portion of a human body and a grounding cable. The grounding cable has an elongated conductive member with a first end for connection to ground potential and a second end for electrically communicating with the body-contacting member. The elongated conductive member is embedded at one end within a resistive material having an electrical conductivity of $10^5$–$10^{12}$ ohms/square. In one embodiment, the body-contacting member is a wrist or ankle strap while the resistive material is a polymer matrix loaded with conductive and/or semiconductive particles. Exemplary particles are selected from carbon, transition metals, and mixtures thereof.

In another aspect, the present invention provides a grounding system within a device for static charge dissipation from an object or person adjacent the device. The grounding system includes a conductive member in electrical communication with ground potential and a resistive material having an electrical conductivity of $10^5$–$10^{12}$ ohms/square positioned between the conductive member and a source of static electricity. In an exemplary embodiment, the grounding system is employed in a telephone headset in which the resistive material comprises a portion of the headset housing. For "hands-free" telephone headsets, the resistive material is positioned in a portion of the headset housing which contacts a portion of the user's head.

DETAILED DESCRIPTION

Figure 1:
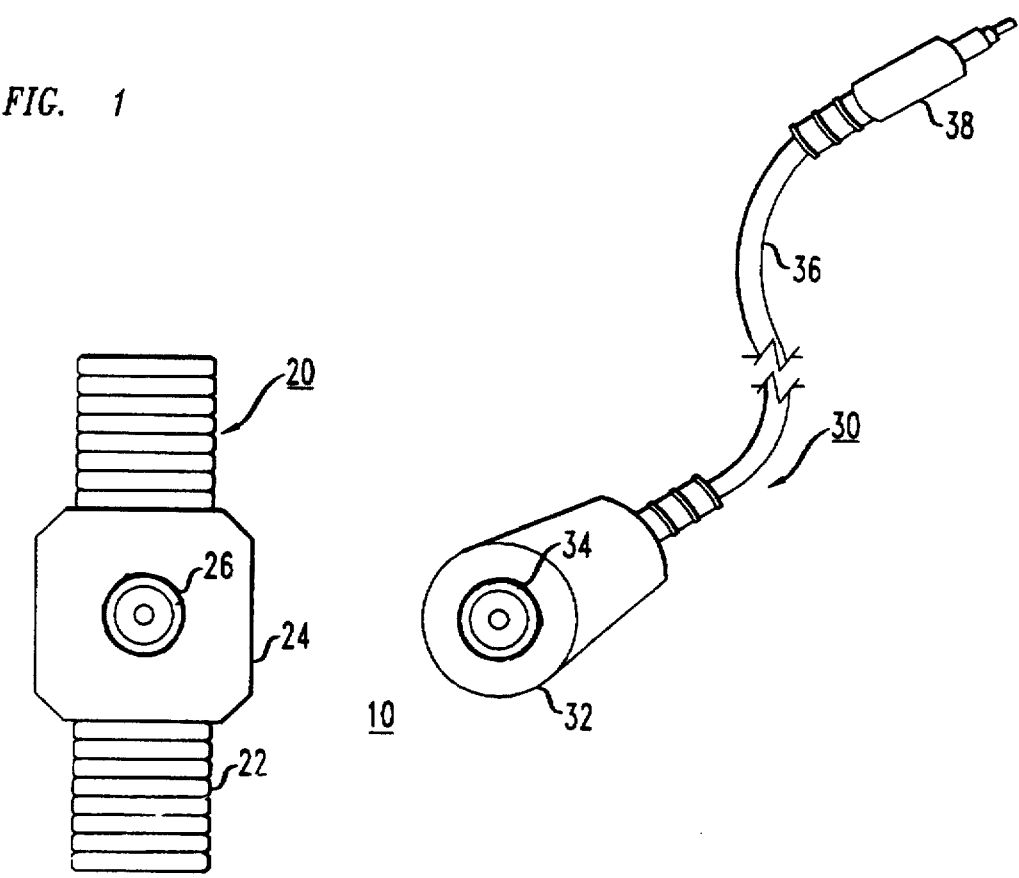
FIG. 1 illustrates a grounding system according to a first embodiment of the present invention.

Turning to the drawings in detail in which like numerals indicate the same or similar elements, FIG. 1 illustrates a grounding system 10 according to a first embodiment of the present invention. Grounding system 10 comprises body-contacting member 20 and grounding cable 30. Body-contacting member 20 is illustratively depicted as a wrist strap, although any element which provides electrical connection with the wearer can be employed as the body-contacting member, including, but not limited to, ankle straps and headsets. Body-contacting member 20 includes flexible wrist band 22 fabricated from a conductive material attached to grounding cable connection element 24. Connection element 24 includes a conductive metallic backing which communicates with fastener 26 through the body of connection element 24. Typically, fastener 26 is a snap configured to receive a mating fastener from grounding cable 30. Grounding cable 30 includes connection element 32 for engagement with body-contacting member 20, elongated conductor 36, and ground connector 38. Connection element 32 includes fastener 34 for interlocking with wrist strap fastener 26.

Figure 2A:
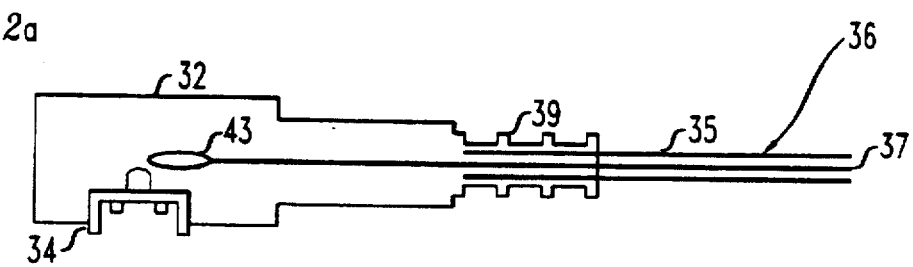
FIGS. 2A and 2B are enlarged side views in partial cross-section of the grounding cable of the grounding system of FIG. 1.

FIG. 2A illustrates a side view in partial cross-section of one embodiment of the grounding cable of FIG. 1. As seen in FIG. 2A, elongated conductor 36 includes wire 37 sheathed in insulative housing 35. Wire 37 passes through strain relief element 39 and terminates in loop 43 within the connection element body 32.

To create an electrical path between wire 37 and connection element fastener 34, connection body 32 and the strain relief element 39 are fabricated from a resistive material. The resistive material conducts electricity, providing a controlled path to ground from the wrist band fastener 26 through grounding cable fastener 34 to wire 37 embedded in the resistive material. Advantageously, this configuration eliminates the need for a resistor positioned within connection element 32. Typically, conventional grounding straps included a resistor in connection element 32. Because of the mechanical strain placed on the wire, contact between the wire and the resistor frequently failed in conventional designs. When this occurred during a production run, static sensitive devices fabricated during that run were destroyed. The present configuration eliminates this problem since there is no small bond between the wire and a resistor which can be broken. Failure of the grounding path in the present system would typically involve physical separation of wire 37 from connecting element 32, as easily observable condition.

Alternatively, the present technique can be employed in conventional wrist strap/grounding cable designs which employ resistors to provide a controlled path to ground. In this embodiment, although a resistor is employed, the connecting element 32 is fabricated from a resistive material. In the event of a resistor/wire connection failure, a controlled path to ground still exists since the wire is embedded in a resistive material.

Figure 2B:
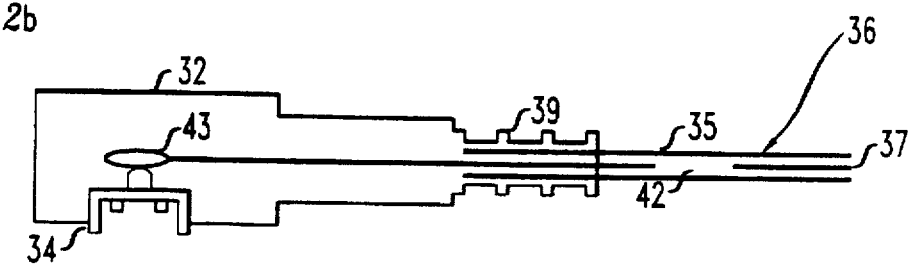
Figure 3:
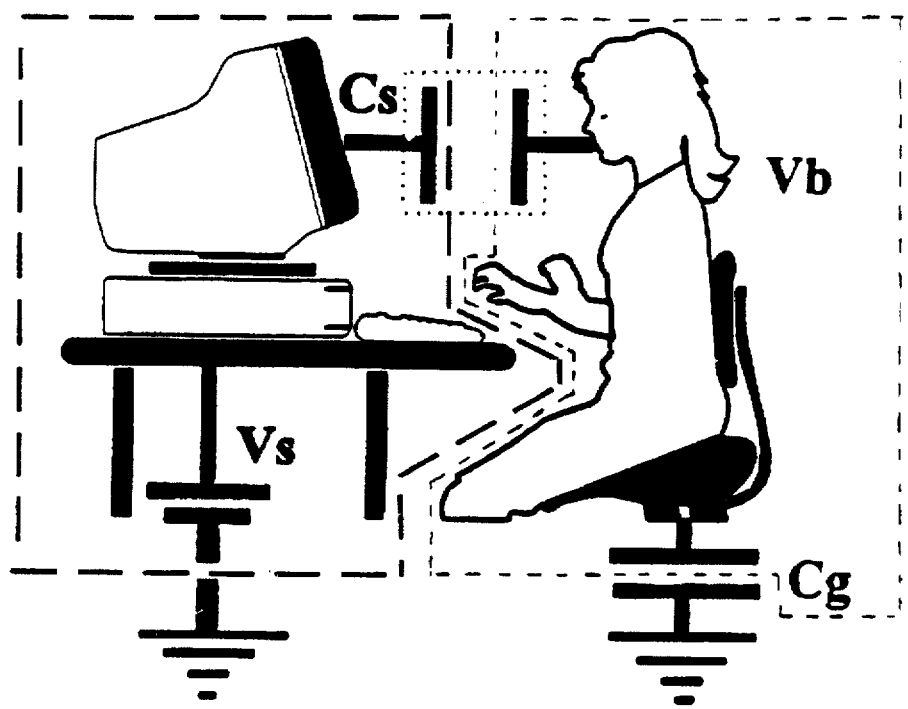
FIG. 3 is a schematic model illustrating charge accumulation through interaction of a user with a video display terminal.

FIG. 2B illustrates a further embodiment of connection element 32 according to the present invention. In this embodiment, wire 37 is embedded in a sheath 35 of resistive material. To provide a controlled path to ground, optionally, a discontinuity 42 is formed in wire 37 such that electrical communication between the two wire ends is made through the resistive material of the sheath. Optionally, the sheath 35 in the cable of FIG. 2A can be made of resistive material, providing a fail-safe in the event of wire breakage.

The resistive material is selected to have a resistivity of $10^5-10^{12}$ ohms/square. Exemplary resistive materials include polymers loaded with conductive or semiconductive particles. Exemplary conductive particles are selected from carbon, metals, semiconductors and mixtures thereof. A particularly advantageous conductive polymer is INTERCEPT™, available from AT&T Corp., having a polyethylene matrix loaded with carbon and/or various transition metal particles including, but not limited to iron, cobalt, manganese, and copper. This material is described in U.S. Pat. No. 5,154,886, the disclosure of which is incorporated by reference herein.

In another aspect, the present invention provides a grounding system for use with electrical devices, particularly, telephone headsets. Surprisingly, it has been discovered that interaction of a user wearing a telephone headset with a cathode ray tube (CRT) from a video display terminal causes accumulation of static electricity, discharge of which is experienced as a painful shock by the wearer of the telephone headset. As schematically illustrated by the dotted region 60 of FIG. 5, electrostatic coupling occurs between CRT and the headset user, modeled as a capacitive network. Assuming that the voltage of the CRT screen, $V_s$, is initially zero, when the CRT is either turned on or turned off $V_s$ swings to a large positive or negative value in a period of about one second. The capacitance $C_s$ between the CRT screen and the user's body and ground along with the capacitance $C_g$ between the ungrounded user's body and ground form a capacitive voltage divider. Thus, the electrostatic potential of the user's body, $V_b$, is given by:

$$V_b = V_s C_s / (C_s + C_g)$$

If the user is very close to or in contact with the CRT, the capacitance $C_s$ is relatively large, resulting in a body potential near that of the CRT. Since there is no flow of charge between the plates of a capacitor, this model illustrates how body potential changes even though charge does not flow to or from the body. The polarization of the body manifests itself in the model as charge transfer through the body from $C_g$ to $C_s$ and vice-versa.

As seen from this model, rapid changes in the potential of a CRT create a field-induced body potential. Typically, this potential is greater than 10 kV. At this potential, an individual coming into contact with a grounded conductor experiences a sudden electrostatic discharge. Such discharge is particularly painful when the grounded conductor is located in a telephone headset, causing the electrical shock to be felt in the face or head.

Figure 4:
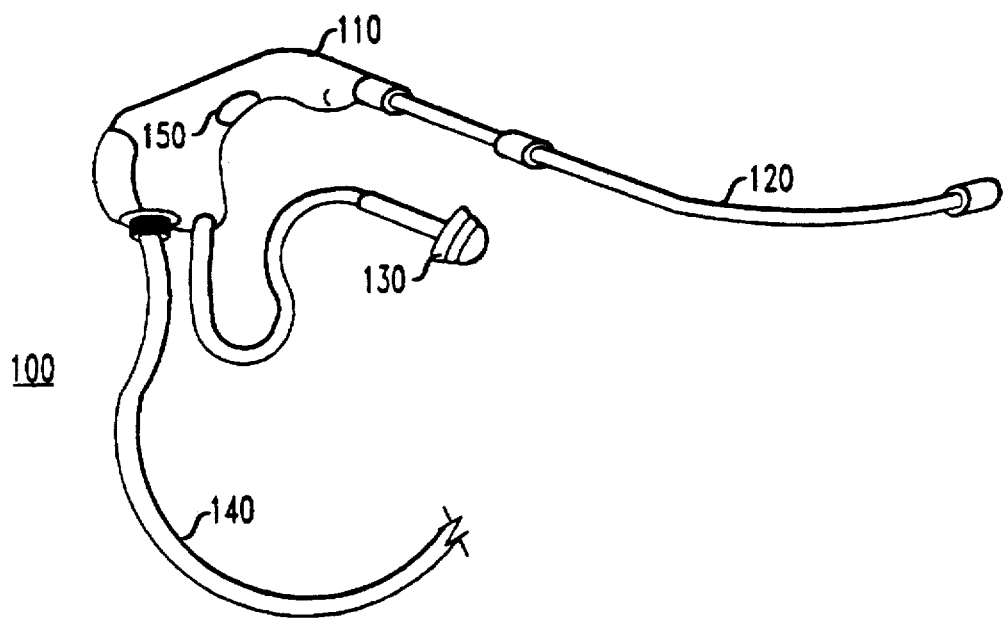
FIG. 4 is a perspective view of a telephone headset incorporating a grounding system according to a further embodiment of the present invention.
Figure 5:
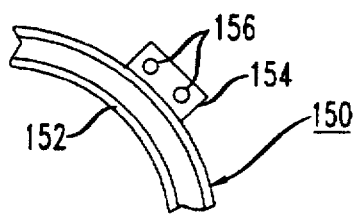
FIG. 5 is a side view of a resistive element employed in the grounding system of the telephone headset of FIG. 4.
Figure 6:
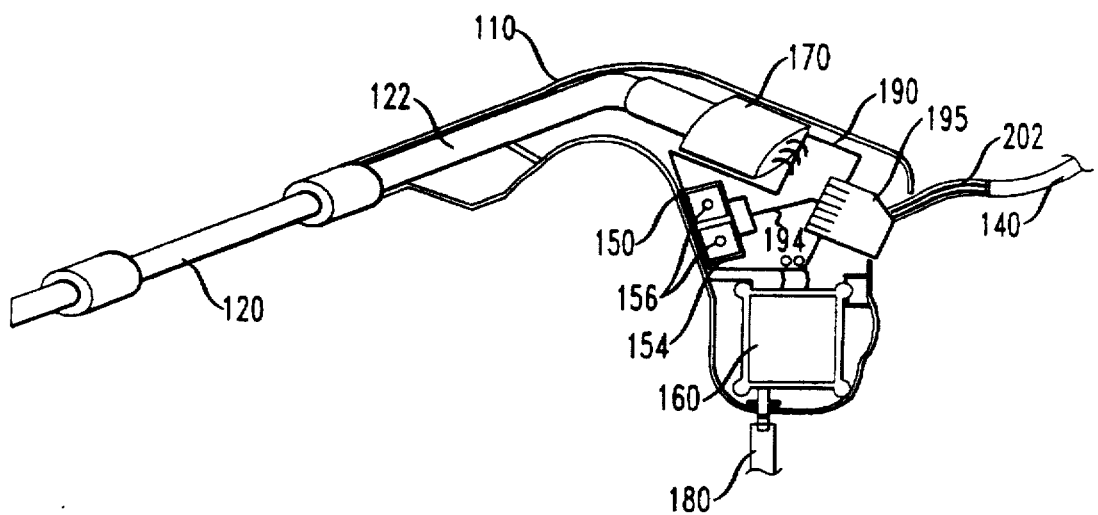
FIG. 6 is an enlarged cross-sectional view of the telephone headset of FIG. 4 illustrating the positioning of the resistive material between the housing and the grounding element.

To solve the problems created by field-induced potentials, it is desirable to maintain the headset user at ground potential. However, a simple grounding path, i.e., a grounding path with no resistive element interposed therein, can create safety issues for the user. One safe way to prevent sudden discharge of accumulated charge is to provide a controlled path to ground within the headset. An example of a controlled path to ground for a "hands-free" telephone headset is illustrated in FIGS. 4-6. FIG. 4 is a perspective view of a STARSET™ telephone headset 100 having ear-mountable capsule portion 110 which includes resistive portion 150, voice tube 120, VERSATIP™ eartip 130, and connecting element 140.

FIG. 5 is an enlarged side view of a portion of headset capsule 150 fabricated from a resistive material having a resistivity between $10^5-10^{12}$ ohms/square. Resistive element 150 includes body-contacting curved exterior portion 152 and planar ground-path connector element 154. As in the previous embodiment, the resistive material is typically selected from polymers which are loaded with conductive or semiconductive particles such as carbon and/or certain transition metals, e.g., those materials described in U.S. Pat. No. 5,154,886. Preferred polymers include solvent-weldable or ultrasonic-weldable polymers such as ABS polymers.

FIG. 6 is a cross-sectional view of headset capsule 110 depicting the incorporation of resistive element 150 in a grounding system. As shown in FIG. 6, capsule portion 110 houses condenser microphone element 170 which receives speech from voice tube 120 through hollow channel 122. Speaker element 160 is also housed within capsule 110, the output of speaker 160 being projected into eartip 130 through conduit 180. Both the speaker 160 and the microphone 170 connect with printed circuit 190 which performs signal processing. The signal input and output from printed circuit 190 are fed through edge connector 195 into leads 200 of headset connection element 140.

As assembled in headset capsule 110, resistive element curved exterior portion 152 contacts the exterior of the user's ear. Resistive element planar portion 154, indicated by the dashed lines in FIG. 6, is positioned beneath printed circuit 190. As illustrated in the FIG. 5, planar element 154 is provided with connection elements 156 in the form of small hemispherical projections for mechanical connection with printed circuit 190. Printed circuit bonding pads 192 contact planar portion 154 and projections 156 for electrical connection to the resistive element. Advantageously, printed circuit 190 is disposed on a pliable polymeric substrate, such as polyamide, in which mating through-holes are provided to facilitate mechanical fastening of elements 156 to the printed circuit. Bonding pads 192, in turn, are joined to circuit line 194, providing a path to the headset grounding lead 202 though a printed circuit bonding pad (not shown) which contacts edge connector 195.

In operation, resistive element 150 provides a path for controlled dissipation to ground of accumulated electrostatic charge, preventing sudden discharges in the form of painful shocks. While the arrangement of FIG. 5 produces the desired dissipation, it is appreciated by those skilled in the art that numerous other configurations also serve to prevent charge accumulation. For example, any portion of the housing which contacts the user's body can be formed from the resistive material. Foams made from the above-described particle-loaded polymers can be used in the resistive element which forms a housing portion. Additionally, any connection which provides a path to ground through the host device is acceptable for charge dissipation. The grounding system can also be employed in other grounded devices which are likely to draw electrical shocks from charged users. The present invention extends to systems in which any portion of a grounded device which is regularly contacted by a user includes a resistive element connected to ground to dissipate static charges as described above.

While the foregoing invention has been described in term of the above detailed embodiments, it will be readily apparent to those skilled in the art that various additions and changes can be made. Accordingly, modifications such as those suggested above, but not limited thereto, are considered to be within the scope of the claimed invention.

We claim:

1. A grounding system for dissipating static electricity comprising:

a body-contacting member which forms an electrical connection with at least a portion of a human body; and a grounding cable having an elongated conductive member with a first end for connection to ground potential, and a second end for electrically communicating with the body-contacting member, at least one end of the elongated conductive member being embedded within a resistive material having an electrical conductivity of $10^5$–$10^{12}$ ohms/square.

2. A grounding system according to claim 1 wherein the body-contacting member is a wrist strap.

3. A grounding system according to claim 1 wherein the body-contacting member is an ankle strap.

4. A grounding system according to claim 1 wherein the resistive material is a polymer matrix loaded with conductive particles, semiconductive particles, or mixtures thereof.

5. A grounding system according to claim 4 wherein the conductive particles are selected from carbon, transition metals, and mixtures thereof.

* * * * *